United States Patent [19]

Inwood

[11] Patent Number: 4,512,978
[45] Date of Patent: Apr. 23, 1985

[54] DERMATOLOGICAL COMPOSITION USEFUL IN THE TREATMENT OF PSORIASIS

[76] Inventor: Louis R. Inwood, 1684 E. 18th St., Brooklyn, N.Y. 11229

[21] Appl. No.: 434,497

[22] Filed: Oct. 15, 1982

Related U.S. Application Data

[63] Continuation of Ser. No. 114,910, Jan. 24, 1980, abandoned, and a continuation of Ser. No. 246,108, Mar. 20, 1981, abandoned.

[51] Int. Cl.³ ............................................. A61K 33/30
[52] U.S. Cl. ................................... 424/145; 514/552; 514/863
[58] Field of Search ...................... 424/145, 322, 312

[56] References Cited

U.S. PATENT DOCUMENTS 2,082,063  6/1937  Khodakoff.

OTHER PUBLICATIONS

Handbook of Nonprescription Drugs, 5th ed., 1977, pp. 305 & 325–341.

*Primary Examiner*—Leonard Schenkman
*Attorney, Agent, or Firm*—Hubbell, Cohen, Stiefel & Gross

[57] ABSTRACT

Dermatological compositions containing urea, zinc oxide, castor oil and starch in a hydrophilic ointment are disclosed. The compositions can be used to treat certain diseases of the nails and skin. The compositions may also contain crude coal tar, hydrocortisone, petrolatum and water.

17 Claims, No Drawings

DERMATOLOGICAL COMPOSITION USEFUL IN THE TREATMENT OF PSORIASIS

This is a continuation of application Ser. Nos. 114,910 and 246,108, filed 1/24/80 and 3/20/81 both abandoned.

BACKGROUND OF THE INVENTION

1. Field of the Invention

The invention relates to dermatological compositions for use in topically treating numerous dermatological diseases and conditions including herpes simplex, herpes zoster, herpes genitalis, acne, acne vulgaris dermatitis, psoriasis, peripherial vascular disease, fungi of the skin, fungi of the nails, ulcerations of the skin, ulcers of the mouth, burns, sunburns, stomatitis, viral ulcers, fulgerations of the skin and, amputation of the skin including both surgical amputation and accidental amputation.

2. Description of the Prior Art

Recurrent herpes simplex is one of the most common and perplexing skin conditions treated by the practicing physician. Basically, herpes simplex is an inflamatory skin disease characterized by the formation of small vesicles in clusters. More specifically, it is believed to be an acute virus disease marked by groups of watery blisters on the skin the mouth and mucus membranes, such as the borders of the lips or the nares and the mucus surface of the genitals. It often accompanies fever. While many different types of chemical formulations have been suggested for use in ameliorating or curing this condition, none of the various proposed solutions has been satisfactory.

A number of the most recent proposed solutions are described in Dermatology, "Topical Therapy of Cutaneous Herpes Simplex" by Michael Jarratt, M.D., pages 10-11, September 1979. In that article, Dr. Jarratt states that "there are several topical agents that may relieve or slightly shorten the duration of individual recurrent lisions. The duration of the individual recurrent lisions, however, continues to be a major problem. Another major problem is that while the lesions eventually heal after the application of one of the currently available topical agents, considerable unsightly scar tissue is formed.

Herpes zoster is another skin disease for which there is no currently available effective treatment. Herpes zoster is an acute inflamatory virus disease of the cerebal ganglia and ganglia posterior of the nerve roots, characterized by groups of small vesicles on inflamatory bases occuring in the cutaneous areas supplied by certain nerve trunks, and associated with nuerological pain. While various treatment for herpes zoster, including radiation therapy, cytosin arabinoside, adenosine Arabinoside (Ara-A), Interferon, Zoster-Immuneglobulin systemic corticosteroids have been used, none of these treatments has been completely satisfactory.

Acne is still another skin disease, which although having received considerable attention, has proved most refractory to effective treatment. Acne generally affects teenagers between the ages of 12 and 18, but also may effect adults. Basically, acne is an inflamatory disease of the sebaceous glands. More specifically, acne vulgaris or common acne is a chronic inflammatory disease of the sebaceious galnds occurring most frequently on the face, back and chest. The inflamed glands form either small pink papules, which sometimes surround comedones so as to have black centers, or else pustules or hypertrophied modules. Often, noticable scar tissue is formed on the skin and remains even after the acne has cleared. While there are numerous formulations for treating acne, none significantly shorten the duration of the disease or prevent scar tissue from being formed.

There are numerous other skin diseases, which although having received considerable attention, have proved most refractory to alleviation or improvement. These skin diseases include, dermatitis, psoriasis, peripheral vascular disease, fungi of the skin, fungi of the nails, ulcerations of the skin, ulcers of the mouth, burns, stomatitis and viral ulcers. Most of these skin diseases are characterized by the formation of groups of small vesicles in clusters on the surface of the skin, ulcers on the surface of the skin and even thickening of the skin.

In an article titled "Dermatologic Therapeutic Survey" in The Journal of the Association of Military Dermatologist, by John L. Aeling, Col., MC, USA, pages 2-4, numerous treatments including topical treatments for many of the above listed skin diseases are disclosed. Such topical treatments include the use of topical zinc oxide for herpes simplex and topical hydrophilic ointment with urea 5% and lactic acid 5% for dry skin. However, none of the topical agents disclosed by Dr. Aeling is chemically similar to the topical agent of the instant application and more importantly none of the topical agents is as effective in treating the various skin conditions as the topical agent of the instant invention.

In addition to the various skin diseases mentioned above, amputation of the skin including both surgical and accidental amputations of the skin create unsightly skin conditions. Surgical amputations include removal of cysts, warts and other unnatural growths on the surface of the skin. Such amputations create unsightly holes and scars on the surface of the skin. Accidental amputations include, for example, the amputation of a portion of a finger (not including the bone). There are no known topical agents, which can be applied to these amputated areas of the skin, which help the skin grow back without the creation of substantial scar tissue.

SUMMARY OF THE INVENTION

I have now found that certain diseases and conditions of the skin and nails can be effectively treated with the composition of my invention. As noted, these diseases and conditions include herpes simplex, herpes zoster, acne, dermatitis, psoriasis, peripheral vascular disease, fungi of the skin, ulcerations of the skin, ulcers of the mouth, burns, sunburns stomatitis, viral ulcers fulgerations and amputations of the skin. In accordance with my invention, there is topically applied to the portion of the body, which exhibits the disease or condition, the therapeutic composition of my invention. This composition comprises urea, zinc oxide, castor oil, starch, hydrophilic ointment and if desired, water, petrolatum, "Aquaphor", crude coal tar and hydrocortisone.

DETAILED DESCRIPTION OF THE PREFERRED EMBODIMENTS

Castor oil is, of course, an old and very well known chemical substance. Traditionally, it has been used as a topical oil for the skin.

I have found that when castor oil is combined in an admixture with starch, zinc oxide, hydrophilic ointment and urea, and provided that the concentrations of the abovementioned components are maintained within specified ranges, the resulting composition exercises a pronounced therapeutic effect on the aforesaid undesirable skin conditions.

In many instances, I have found that topical application of my composition to regions of the body afflicted with one of the aforesaid skin conditions, results in the rapid healing of watery blisters, lesions, ulcers, or the like which are exhibited by the particular skin condition, without the creation of scar tissue. The reaction mechanism or the scientific explanation as to precisely what accounts for such rapid healing without the creation of scar tissue is presently unknown.

As regards the therapeutic composition of my invention, castor oil is the most active component. However, castor oil, alone, does not produce the desired therapeutic effect. In addition, I provide for the presence of at least four other components, including starch, zinc oxide, hydrophilic ointment and urea. Crude coal tar, water, petrolatum, "Aquaphor", and cortisone can also be added, if desired. Provided that the concentrations of the components are maintained within specific ranges, the composition exhibits the desired therapeutic effect.

While it is not certain, castor oil may obtain its therapeutic effect from its most active component, sodium ricinoleate, which has been found to contain prostaglardins E and F. The therapeutic effect of prostaglandins has recently been recognized in numerous studies. In general, the castor oil is present in an amount of from about 1 to 20% by weight of the composition. However, a more desirable range is of from about 1 to 10% by weight of the composition. A still more desirable range is of from about 2 to 5% by weight of the composition.

As regards the starch, various types of grain starches may be employed, including potato starch, rice starch, wheat starch and corn starch. While any one of the abovementioned starches may be employed in the composition of the instant invention, corn starch is most preferred. In general, the starch should be present in an amount of from about 1 to 30% by weight, in the final composition. A more desirable range is of from about 1 to 20% by weight of the composition and a still more preferred range is of from about 5 to 15% by weight of the final composition.

Zinc oxide is also employed in the composition of the instant invention. Zinc oxide produces a soothing effect on the skin and, in general, should be present in an amount of from about 1 to 20% by weight of the composition. A more desirable range is of from about 1 to 7% by weight of the composition. It appears that in most instances, the optimum zinc oxide concentration is of from about 1 to 3% by weight, of the composition.

Urea, which is also present in the composition, acts as a moisturizer. In general, it is present in an amount of from about 5 to 40% by weight of the composition. While urea may be present in any amount within this range, a more desirable range is of from about 5 to 20% by weight of the final composition. However, the preferred range is of from about 10 to 25% by weight of the composition.

The base for the composition generally comprises hydrophilic ointment. Specifically, hydrophilic ointment is an oil-in-water type dispersion of stearyl alcohol and white petrolatum in a medium of propylene glycol and water containing sodium lauryl sulfate as a surface active agent and methylparaben and propylparaben as antimicrobial preservatives. Hydrophilic ointment is desirable since it is readily removed from the skin and clothing by washing with water. In general, hydrophilic ointment is present in an amount of from about 1 to 90% by weight of the composition. A more desirable range is of from about 1 to 50% by weight of the composition, and a still more desirable amount is of from about 28 to 41% by weight of the composition.

If desired "Aquaphor" (Aquaphor is a super-fatted soap chemically available from Duke), can be substituted for a portion of the hydrophilic ointment that is normally used. Thus, if "Aquaphor" is employed it is generally present in an amount of from about 1 to 40% by weight of the composition and more desirable in an amount of from about 10 to 20% by weight of the composition.

In addition to Aquaphor, petrolatum can also be substituted for a portion of the hydrophilic ointment to form the base. If petrolatum is employed it is generally present in an amount of from about 1 to 20% by weight of the composition and more desirable in an amount of from about 10 to 15% by weight of the composition.

While not required, water may also be added to the composition of the instant invention. Basically, if water is present the final composition can be produced without the use of a high speed mixing apparatus. The precise method of making the composition both with and without water will be described in detail hereinafter. Generally, if water is employed, it is present in an amount of from about 1 to 60% by weight of the composition. However, a more desirable range is of from about 1 to 40% by weight of the composition, and a still more desirable amount is of from about 25 to 35% by weight of the composition.

Also, while not absolutely necessary, crude coal tar may be added to the composition. The crude coal tar produces an anaesthetic effect and is present in an amount of from about 1/100 to 15% by weight of the composition. It is more desirable, however, to have of from about 1/100 to 10% crude coal tar. A still more desirable amount is of from about 1/100 to 7% by weight of the composition.

Hydrocortisone may also be added to the composition in an amount of from about 0.1% to 5% by weight of the aqueous composition, and preferably in an amount of from about 1 to 3% by weight of the composition. Hydrocortisone has an effect on carbohydrate and protein metabolism and is used as an anti-inflammatory.

Various perfumes and colorants may also be added to make the composition of my invention pleasing in both smell and appearance.

In the case of a person suffering from herpes simplex, I have found that topical application of the composition of my invention will result in the rapid disappearance of watery blisters, or the like, which accompany this skin disease. Moreover, the watery blisters or the like heal without the creation of any scar tissue. This is very important, since herpes simplex is a periodically recurring skin disease, which usually creates unsightly scar tissue around the mouth of the person suffering from the disease.

Topical treatment of the particular area affected can be as often as hourly, or as little as daily, and the treatment should be continued until the watery blisters or the like completely disappear. In most instances, the affected area will be completely cleared within two to three days.

Topical treatment of the other aforesaid skin diseases, which are characterized by watery blisters, ulcers or the like on the surface of the skin and mouth is similar to the treatment discussed with respect to herpes simplex.

In the case of a person suffering from either a surgical or accidental amputation of a portion of the skin, I have found that the composition of my invention should be copiously applied to the affected area and, thereafter, wrapped in a bandage, to thereby seal the ointment against the skin. The length of time the area should be bandaged depends upon the severity of the amputation being treated. Remarkably, when the amputated area is treated in this manner, the skin grows back with little or no scar tissue.

While other methods may be used to prepare the composition of my invention, I have found that the following method is most desirable. First, if crude coal is employed, it is admixed with castor oil. Then, zinc oxide is added and mixed together with the castor oil and crude oil tar (if employed). Next, hydrophilic ointment is added and the formulation is vigorously mixed. If "Aquaphor" and/or petrolatum are employed to replace a portion of the hydrophilic ointment, as described previously, they too are added at this stage of the procedure. After this is done, the starch and urea are added and admixed with the other components. Finally, if hydrocortisone is employed it is added and admixed. The final mixture must then be thoroughly mixed by a high speed mixer. A high speed mixer, however, will not be necessary if water is employed. A normal low speed mixer will be all that is required. Generally, water is added after all the other components have been admixed.

Specific examples of some preferred formulations of my invention are as follows:

EXAMPLE I

| Component | Amount |
| --- | --- |
| urea | 10 gm |
| zinc oxide | 1 gm |
| castor oil | 2 cc |
| corn starch | 10 gm |
| hydrophilic ointment | 76 cc |

EXAMPLE II

| Component | Amount |
| --- | --- |
| urea | 10 gm |
| zinc oxide | 1 gm |
| castor oil | 2 cc |
| corn starch | 10 gm |
| hydrophilic ointment | 41 cc |
| water | 35 cc |

EXAMPLE III

| Component | Amount |
| --- | --- |
| urea | 10 gm |
| crude coal tar | 3 gm |
| zinc oxide | 2 gm |
| castor oil | 2 cc |
| corn starch | 10 gm |
| hydrophilic ointment | 74 cc |

EXAMPLE IV

| Component | Amount |
| --- | --- |
| urea | 20 gm |
| crude coal tar | 3 gm |
| zinc oxide | 2 gm |
| castor oil | 4 cc |
| corn starch | 10 gm |
| hydrophilic ointment | 61 cc |

EXAMPLE V

| Component | Amount |
| --- | --- |
| urea | 20 gm |
| crude coal tar | 3 gm |
| zinc oxide | 2 gm |
| castor oil | 4 cc |
| corn starch | 10 gm |
| hydrophilic ointment | 31 cc |
| water | 30 cc |

EXAMPLE VI

| Component | Amount |
| --- | --- |
| urea | 20 gm |
| crude coal tar | 4 gm |
| zinc oxide | 2 gm |
| castor oil | 4 cc |
| corn starch | 10 gm |
| hydrophilic ointment | 60 cc |

EXAMPLE VII

| Component | Amount |
| --- | --- |
| urea | 20 gm |
| zinc oxide | 2 gm |
| crude coal tar | 5 gm |
| castor oil | 5 cc |
| corn starch | 10 gm |
| hydrophilic ointment | 58 cc |

EXAMPLE VIII

| Component | Amount |
| --- | --- |
| urea | 20 gm |
| zinc oxide | 2 gm |
| crude coal tar | 10 gm |
| castor oil | 5 cc |
| corn starch | 10 gm |
| hydrophilic ointment | 53 cc |

EXAMPLE IX

| Component | Amount |
| --- | --- |
| urea | 20 gm |
| crude coal tar | 10 gm |
| zinc oxide | 2 gm |
| castor oil | 5 cc |
| corn starch | 10 gm |
| hydrophilic ointment | 28 cc |
| water | 25 cc |

EXAMPLE X

| Component | Amount |
|---|---|
| urea | 20 gm |
| crude coal tar | 3 gm |
| zinc oxide | 2 gm |
| castor oil | 4 cc |
| corn starch | 10 gm |
| hydrophilic ointment | 31 cc |
| water | 29 cc |
| hydrocortisone | 1 cc |

Variations can, of course, be made without departing from the spirit and scope of my invention.

Having thus described my invention, what is desired to be secured by Letters Patent and hereby claimed is:

1. A dermatological composition comprising 1–20% castor oil, 3–10% crude coal tar, 1–30% starch, 1–20% zinc oxide and 5–40% urea in a hydrophilic ointment base; all percentages expressed by weight of the final composition.

2. A composition according to claim 1, wherein castor oil comprises 2–5% thereof.

3. A composition according to claim 2, additionally comprising 0.1% to 5% hydrocortisone.

4. A composition according to any of claims 1, 2, and 3, additionally comprising 1–60% water.

5. A composition according to any of claims 1, 2, and 3, additionally comprising 1–20% petrolatum.

6. A composition according to claim 5, additionally comprising 1–60% water.

7. A composition according to claim 1, wherein starch is corn starch.

8. A composition according to claim 2, having the following formulation: 20% urea, 3% crude coal tar, 2% zinc oxide 4% castor oil, 10% starch, and 61% hydrolphilic ointment.

9. A composition according to claim 4, having the following formulation: 20% urea, 3% crude coal tar, 2% zinc oxide, 4% castor oil, 10% starch, 31% hydrophilic ointment and 30% water.

10. A composition according to claim 2, having the following formulation: 20% urea, 4% crude coal tar, 2% zinc oxide, 4% castor oil, 10% starch and 60% hydrophilic ointment.

11. A composition according to claim 2, having the following formulation: 20% urea, 5% crude coal tar, 25 zinc oxide, 5% castor oil, 10% starch, and 58% hydrophilic ointment.

12. A composition according to claim 2, having the following formulation: 20% urea, 10% crude coal tar, 2% zinc oxide, 5% castor oil, 10% starch, and 53% hydrophilic ointment.

13. A composition according to claim 4, having the following formulation: 20% urea, 10% crude coal tar, 2% zinc oxide, 5% castor oil 10% starch, 28% hydrophilic ointment and 25% water.

14. A composition according to claim 4, having the following formulation: 20% urea, 3% crude coal tar, 2% zinc oxide, 4% castor oil, 10% starch, 31% hydrophilic ointment, 29% water and 1% cortisone.

15. A method of treating a patient afflicted with psoriasis, said method comprising topically applying to the affected area a therapeutically effective amount of the composition according to claim 1.

16. A method of treating a patient afflicted with psoriasis, said method comprising topically applying to the affected area a therapeutically effective amount of the composition according to claim 2.

17. A method of treating a patient afflicted with psoriasis, said method comprising topically applying to the affected area a therapeutically effective amount of the composition according to claim 3.

* * * * *